(12) United States Patent
Ravikumar et al.

(10) Patent No.: US 10,765,443 B2
(45) Date of Patent: Sep. 8, 2020

(54) NEEDLESCOPIC SCISSOR END EFFECTOR AND METHODS OF USE

(71) Applicant: TELEFLEX MEDICAL INCORPORATED, Morrisville, NC (US)

(72) Inventors: Sundaram Ravikumar, Briarcliff Manor, NJ (US); Guy Osborne, Trumbull, CT (US)

(73) Assignee: TELEFLEX MEDICAL INCORPORATED, Morrisville, NC (US)

( * ) Notice: Subject to any disclaimer, the term of this patent is extended or adjusted under 35 U.S.C. 154(b) by 349 days.

(21) Appl. No.: 15/329,370

(22) PCT Filed: Jul. 27, 2015

(86) PCT No.: PCT/US2015/042233
§ 371 (c)(1),
(2) Date: Jan. 26, 2017

(87) PCT Pub. No.: WO2016/018806
PCT Pub. Date: Feb. 4, 2016

(65) Prior Publication Data
US 2017/0215908 A1    Aug. 3, 2017

Related U.S. Application Data

(60) Provisional application No. 62/029,633, filed on Jul. 28, 2014.

(51) Int. Cl.
*A61B 17/32* (2006.01)
*A61B 17/3201* (2006.01)
(Continued)

(52) U.S. Cl.
CPC .. *A61B 17/320016* (2013.01); *A61B 17/2909* (2013.01); *A61B 17/3201* (2013.01);
(Continued)

(58) Field of Classification Search
CPC .............. A61B 17/2909; A61B 17/295; A61B 17/3201; A61B 2017/2901;
(Continued)

(56) References Cited

U.S. PATENT DOCUMENTS 5,172,700 A    12/1992  Bencinci et al.
5,290,309 A    3/1994   Kothe
(Continued)

FOREIGN PATENT DOCUMENTS

CN    102316814 A    1/2012
CN    102573672 A    7/2012
(Continued)

*Primary Examiner* — Martin T Ton
(74) *Attorney, Agent, or Firm* — Baker & Hostetler LLP

(57) ABSTRACT

A needlescopic scissors end effector assembly includes a pair of jaws or blades pivotable to perform a cutting or shearing operation. The scissors end effector assembly includes a cannula having a diameter between about 1 mm to 5 mm and a needle tip configured for percutaneous operation. The pair of jaws or blades includes cam profile surfaces to interact with an opening defined with the needle tip to actuate opening and closing of the pair of jaws or blades and to prevent backlash effect during the opening and closing of the pair of jaws or blades.

20 Claims, 11 Drawing Sheets

(51) Int. Cl.
*A61B 17/29* (2006.01)
*A61B 18/12* (2006.01)
*A61M 5/34* (2006.01)
*A61B 17/00* (2006.01)
*A61B 18/00* (2006.01)

(52) U.S. Cl.
CPC ............... *A61B 18/12* (2013.01); *A61M 5/34* (2013.01); *A61B 2017/00345* (2013.01); *A61B 2017/00929* (2013.01); *A61B 2017/2902* (2013.01); *A61B 2017/2933* (2013.01); *A61B 2018/00595* (2013.01); *A61B 2018/00601* (2013.01)

(58) Field of Classification Search
CPC .... A61B 2017/2902; A61B 2017/2912; A61B 2017/2913; A61B 2017/2926; A61B 2017/2932; A61B 2017/2933; A61B 2017/2939; A61B 2017/2941; A61B 2017/2947; A61B 2018/00601; A61B 18/1447; A61B 2018/1445; A61B 2018/146
USPC .......................................... 606/174, 205–208
See application file for complete search history.

(56) References Cited

U.S. PATENT DOCUMENTS

| | | | |
|---|---|---|---|
| 5,490,861 A | 2/1996 | Kratsch et al. | |
| 5,549,627 A * | 8/1996 | Kieturakis | A61B 17/29 606/206 |
| 5,626,597 A * | 5/1997 | Urban | A61B 17/34 606/159 |
| 6,024,750 A | 2/2000 | Mastri et al. | |
| 6,086,606 A * | 7/2000 | Knodel | A61B 17/29 606/174 |
| 6,206,903 B1 | 3/2001 | Ramans | |
| 6,818,007 B1 * | 11/2004 | Dampney | A61B 17/29 606/205 |
| 9,492,163 B2 * | 11/2016 | Bagaoisan | A61B 17/0485 |
| 2004/0098041 A1 | 5/2004 | Wagner et al. | |
| 2008/0140022 A1 * | 6/2008 | Pond | A61M 25/065 604/272 |
| 2010/0016884 A1 | 1/2010 | Ravikumar | |
| 2010/0292724 A1 * | 11/2010 | Ravikumar | A61B 17/221 606/185 |
| 2011/0144768 A1 | 6/2011 | Slater | |
| 2011/0213366 A1 * | 9/2011 | Baldwin | A61B 17/29 606/49 |
| 2012/0083814 A1 | 4/2012 | Kessler | |
| 2013/0023875 A1 * | 1/2013 | Harris | A61B 18/1447 606/47 |
| 2013/0165907 A1 | 6/2013 | Attar et al. | |

FOREIGN PATENT DOCUMENTS

| | | |
|---|---|---|
| CN | 103690222 A | 4/2014 |
| DE | 20 2007 009315 U1 | 8/2007 |
| JP | 5-115488 A | 5/1993 |
| WO | 2012160715 A1 | 11/2012 |
| WO | 2013/120491 A1 | 8/2013 |

* cited by examiner

NEEDLESCOPIC SCISSOR END EFFECTOR AND METHODS OF USE

CROSS-REFERENCE TO RELATED APPLICATION

This patent application is a national stage entry of PCT/US2015/042233, filed on Jul. 27, 2015, which claims priority to U.S. Provisional Patent Application No. 62/029,633, filed Jul. 28, 2014, each of the disclosures of which are hereby incorporated by reference in their entirety.

TECHNICAL FIELD

The present disclosure relates to surgical instruments and methods of their use, and more particularly to minimally invasive surgical instruments including a scissors end effector and methods of use in surgery.

Examples of minimally invasive surgical assemblies and related equipment are described in U.S. Pat. No. 7,766,937 to Ravikumar, U.S. Pat. No. 8,230,863 to Ravikumar et al., U.S. Pat. No. 8,313,507 to Ravikumar, U.S. Pat. No. 8,133,255 to Ravikumar et al., U.S. patent application Ser. No. 11/685,522 to Ravikumar et al. (published as U.S. Patent Pub. No. 2007/0250112), U.S. patent application Ser. No. 12/503,035 to Ravikumar (published as U.S. Patent Pub. No. 2010/0016884), U.S. patent application Ser. No. 11/610,746 to Ravikumar et al. (published as U.S. Patent Pub. No. 2007/0282170), and U.S. patent application Ser. No. 12/689,352 to Ravikumar et al. (published as U.S. Patent Pub. No. 2010/0292724), all of which patents, applications, and publications are incorporated by reference herein in their entireties.

DESCRIPTION OF RELATED ART

Over the last two decades, minimally invasive surgery has become the standard for many types of surgeries which were previously accomplished through open surgery. Minimally invasive surgery generally involves introducing an optical element (e.g., laparoscopic or endoscope) through a surgical or natural port in the body, advancing one or more surgical instruments through additional ports or through the endoscope, conducting the surgery with the surgical instruments, and withdrawing the instruments and scope from the body. In laparoscopic surgery (broadly defined herein to be any surgery where a port is made via a surgical incision, including but not limited to abdominal laparoscopy, arthroscopy, spinal laparoscopy, etc.), a port for a scope is typically made using a surgical trocar assembly.

The trocar assembly often includes a port, a sharp pointed element (trocar) extending through and beyond the distal end of the port, and at least in the case of abdominal laparoscopy, a sealing valve on the proximal portion of the port. The term trocar typically includes a combination of cooperating elements such as a cannula, a seal housing and an obturator. First the obturator cuts or pierces the body wall so that the cannula may be inserted. The cannula defines a pathway through a body wall through which the surgical instruments are placed. Finally the seal housing provides an isolation of the cannula so that if insufflation is employed the body region remains distended and sealed. All three components are usually fitted together and used as a single unit for passage by one or more surgical instruments through the body wall and into a body cavity.

Laparoscopic surgery typically begins as the surgeon inserts a large bore needle through a body wall and into the internal region associated with the body wall. Next, an inflation or insufflation gas is pumped into the internal region until it is properly distended. The body wall and internal region are now ready for insertion of trocars.

Typically, a small incision is made in the skin at a desired location in the patient. The incision may be made via a scalpel or other sharp instrument. The trocar assembly, with the trocar extending out of the port, is then forced through the incision via the obturator which cuts or pierces the body wall, thereby widening the incision and permitting the port to extend through the incision, past any fascia, and into the body (cavity). The trocar is then withdrawn, leaving the port in place.

If not already distended, an insufflation element may be attached to the trocar port in order to insufflate the surgical site. An optical element may then be introduced through the trocar port. Additional ports are then typically made so that additional laparoscopic instruments may be introduced into the body.

Trocar assemblies are manufactured in different sizes. Typical trocar port sizes include diameters of about 5 mm, 10 mm, and 12 mm, which are sized to permit variously sized laparoscopic instruments to be introduced therethrough including, e.g., graspers, dissectors, staplers, scissors, suction/irrigators, clamps, forceps, biopsy forceps, etc. While 5 mm diameter trocar ports are relatively small, in some circumstances where internal working space is limited (e.g., children), it is difficult to place multiple 5 mm diameter ports in the limited area. In addition, 5 mm diameter trocar ports tend to limit movement of instruments inside the abdominal cavity to a great extent. Such a conventional 5 mm diameter trocar has a sealing valve and sealing mechanism and therefore the opening for the surgical instrument is limited.

Further, while laparoscopic surgery has reduced the trauma associated with various surgical procedures and has concomitantly reduced recovery time from these surgeries, there always remains a desire in the art to further reduce the trauma to the patient.

One area of trauma associated with laparoscopic surgery identified by the inventor hereof as being susceptible of reduction are the scars which result from the trocar ports used. In many laparoscopic surgeries, three or more trocar incisions are made. For example, in laparoscopic hernia repair surgery, four trocar incisions are typically made, with one incision for insufflating the abdomen via a placed trocar and using such trocar for inserting the optical device, two incisions for placing trocar ports for inserting graspers therethrough, and a fourth port for passing a stapler therethrough. Those skilled in the art and those who have undergone surgical procedures understand that even the 5 mm diameter trocar ports leave holes which must be stitched and which result in scars. Scar tissue may affect the internal portion of the fascia as well as the cosmetic appearance of the skin, which may be detrimental for the patient or even a surgeon if that area of the skin is subject to a later incision or medical procedure. Thus a need exists for surgical methods which include less trocars and more self-inserting surgical instruments, or end-effectors for surgical instruments, such as replacing the one or both of the second and third trocars referred to above in a conventional laparoscopic hernia surgery.

A second area of trauma associated with laparoscopic surgery relates to trauma resulting from the manipulation (e.g., angling) of the trocar ports required in order to conduct the surgery due to inexact placement. Angling of the port can cause tearing at the incision periphery. Such tearing can lead to extensive scar tissue and in general an extension of the incision area. Thus a need exists for a self-inserting surgical instrument or end effector on a surgical instrument which reduces or eliminates tearing of an incision point due to manipulation or angling of a cannula of such surgical instrument or end effector.

A further problem with surgical instruments such as scissors is inadvertent penetration in tissue and resulting scarring or even more serious complications during the surgery if other tissue is nicked or penetrated unintentionally. This problem may also occur if the surgical instrument has an unprotected needle tip and the needle inadvertently penetrates or nicks tissue or organs. Indeed, placing a sharp instrument such as an inflation needle or trocar obturator or surgical scissors through a body wall and into an associated internal region comes with considerable risk. The human abdomen, for example, is a tightly packed region that is filled with delicate structures and organs. There is no open space between the abdominal wall and those structures or organs until inflation gas is inserted and a pneumoperitoneum is established. Great care must be taken when placing inflation needles so as to avoid penetration of intestine, bowel or other structures. Even after insufflation is established, there is a risk of injury during placement of additional sharp instruments (such as scissors end effectors or needle tips) through the distended body wall. The body wall is comprised of skin, muscle, fat and a thin membrane. The wall may be thick, muscular and tough or it may be lean and soft and great force is needed to penetrate it, which force may lead to inadvertent cutting of other tissue or organs. Thus a need exists for a safety feature on a scissors end effector or surgical instrument including scissors end effectors to reduce or prevent inadvertent tissue penetration or cutting.

To combat the need for such force of insertion of a typical trocar, some surgeons have also used a technique referred to as a "cut down" procedure where successive small incisions are made until the body wall is cut through, at which time a blunt trocar or a trocar obturator is inserted with a certain level of force. This process may incur less force but it is time-consuming and may leave a deeper and larger scar.

Further, the use of conventional scissors in laparoscopic surgical instruments have many disadvantages such as recoil upon actuation and limited scope of the cutting area. Indeed, conventional surgical scissors are actuated via a formed wire that passes through opposing slots in the scissor blades, or through a toggle linkage or plunger mechanism. In all cases, manufacturing tolerances require clearance between the mating components which results in backlash when the scissors are alternated between opening and closing motions. This mechanical backlash means that when surgeon opens and closes his or her hand to change direction of the scissors there is lost motion for a period where the device handpiece, such as a surgical instrument handle, is being manipulated but the scissor blades remain static. This results in reduced control of the scissors by the surgeon. A common surgical technique is to take down tissue and organs using a progressive series of precise small snips using the scissor tips, and mechanical backlash within the device or instrument can result in a significant loss of surgeon control during cutting. Such backlash during actuation of the scissor blades or jaws may cause trauma to the tissue within the body cavity and possible nick of vital organs. Further, the backlash may affect the surgeon in that the surgeon must position the distal tip of the closed scissors end effectors within a fraction of a millimeter of the desired location for cutting, however, because of friction and backlash in the way conventional scissors are forced open via a wire or plunger mechanism achieving this level of accuracy is difficult.

For example, when conventional scissors end effectors are actuated from the closed standard position into an open position for cutting, and then further actuated to force the two blades, shears or jaws together to cut, the tension on the surgical instrument causes the instrument to be pulled taught and the instrument naturally assumes the shortest path through the cannula of the surgical instrument. When the wire, toggle or plunger used to actuate the scissors end effectors are pushed forward, friction causes it to assume the longest path through the cannula. Thus, backlash or lost motion is experienced by the surgeon when he/she attempts to actuate the scissors end effectors of the surgical instrument. The surgeon has to accommodate for the backlash and therefore must either overcompensate or undercompensate for the target location of the cutting by several millimeters. If this backlash can be reduced or eliminated, the manipulation of the distal end of the scissors end effectors of the surgical instrument can be made much easier and more accurate, then the surgeon can achieve a more accurate surgery and a quicker surgery time.

In view of the above, the inventors of the present disclosure have identified that a need exists for reducing or eliminating backlash during operation of surgical scissors. The inventors of the present disclosure have also further identified a need for a surgical instrument end effector which both cuts and coagulates tissue during a surgery. For instance, during many surgical procedures, the surgeon may use scissors to dissect or cut certain tissue or organs and thereafter remove the scissors end effector or scissors surgical instrument and then insert a different electrical cauterization end effector or electrical cauterization surgical instrument. Multiple exchanges of the various end effectors or surgical instruments may be required during such a surgical procedure, resulting in longer surgery time, increased chance of infection by exposure of the body cavity and patient fascia with each exchange, and increased chance of inadvertent cutting. The inventors of the present disclosure contemplate a single end effector or surgical instrument which achieves both cutting and electrical cauterization of tissue during surgery procedures to address the above noted issues in conventional scissors surgical instrument.

There continues to be a need in the art for surgical scissors which reduce trauma to the patient, reduce complications to the patient, do not lead to extension of the incision area, do not lead to increased scar tissue generation, reduce patient recovery time and pain, are easy to make and use, more accurate with less or no backlash, and improve safety while reducing costs to health care providers and patients and reducing the surgical time for a procedure which in turn may reduce costs and complications.

The inventors of the present disclosure have further identified a need for a scissors end effector which is easier to insert through a body wall. Additionally, a further need exists for a scissors end effector which is self-inserting into a body wall.

Other advantages of the present invention will become apparent from the following description and appended claims.

SUMMARY

According to one aspect, the disclosure describes a scissors end effector assembly. The scissors end effector assembly comprises a cam tube extending in a longitudinal direction, the cam tube having a proximal end and a distal end.

The further scissors end effector assembly comprises a clevis attached to the distal end of the cam tube, the clevis including an upper arm and a lower arm and a cam bushing defining an upper slot and a lower slot for slidably receiving the upper arm and the lower arm, respectively. The scissors end effector assembly also comprises a top shear and a bottom shear pivotally mounted between the upper arm and the lower arm.

According to one aspect, the disclosure describes a needlescopic surgical device comprising a handle assembly having a trigger handle pivotally attached to the handle assembly, and having a hub for receiving an end effector assembly. The needlescopic surgical device further comprises a scissors end effector assembly including a cam tube extending in a longitudinal direction, a clevis attached to a distal end of the cam tube, the clevis including an upper arm and a lower arm, a cam bushing defining an upper slot and a lower slot for slidably receiving the upper arm and the lower arm, respectively, and a top shear and a bottom shear pivotally mounted between the upper arm and the lower arm. The at least the cam tube of the scissors end effector assembly is inserted into the hub of the handle assembly.

According to one aspect, the disclosure describes a method of using a scissors end effector assembly including a pair of shears, a clevis, a fastener, a cam bushing, a needle tip, and a cam tube. The method may include a step of inserting at least the cam tube of the scissors end effector assembly into a hub of a handle assembly. The method comprises a step of actuating a trigger handle of the handle assembly to advance the needle tip over the pair of shears and to place the pair of shears in a closed position. The method may include a step of puncturing, with the needle tip, through a body wall and into a body cavity such that at least the pair of shears are within the body cavity. The method may include a step of retracting the needle tip to advance the pair of shears towards an open position. The method may include a step of cutting a target by at least partially advancing the needle tip over the pair of shears and moving the pair of shears from the open position toward the close position.

DETAILED DESCRIPTION

Figure 1:
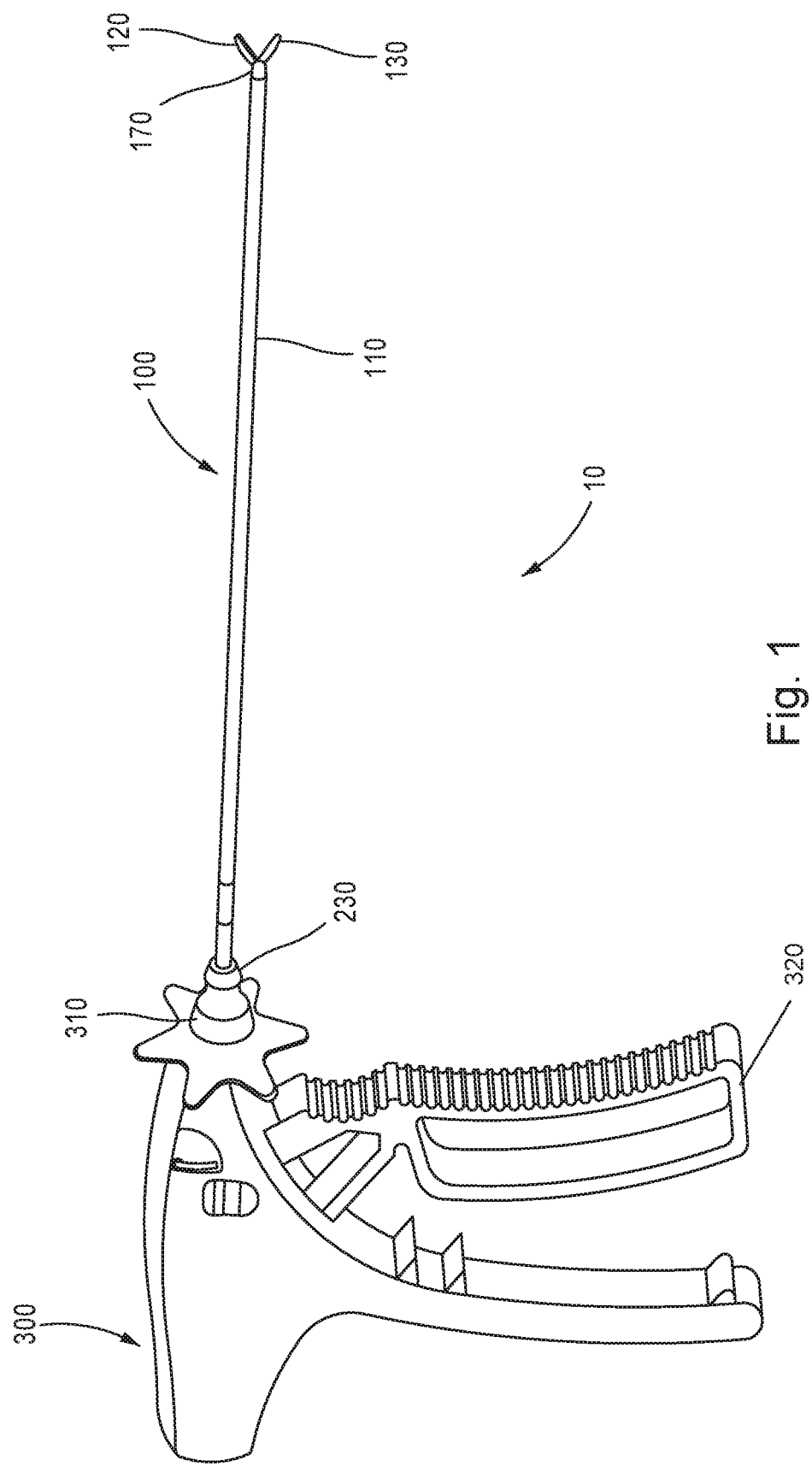
FIG. 1 shows a perspective view of an exemplary surgical instrument including a scissors end effector assembly in accordance with aspects of the disclosure.

Now referring to the drawings, wherein like reference numerals refer to like elements, exemplary aspects of the present disclosure will now be discussed with reference to FIGS. 1-12. In one aspect, the needlescopic scissors end effector of the present disclosure provides a low-cost, easy to manufacture, scissors end effector which may be used, for example, for minimally invasive surgical procedures to reduce trauma to a patient, improve control by reducing or eliminating backlash, reduce surgery time, and/or provide cutting and electrical cauterization in a single end effector assembly unit.

Referring to FIG. 1, a surgical instrument 10 may include a scissors end effector assembly 100 operatively attached to a handle assembly 300, and the scissors end effector assembly 100 may be secured to the handle assembly 300 via a lock hub 230. The end effector assembly 100 may include a cannula 110 with a needle tip 170, a top jaw or shear 120, and a bottom jaw or shear 130. As will be described in further detail below, the scissors end effector assembly 100 may include at least one or more of a spring, a cam tube, a cam bushing, a clevis, a fastener, and a needle tip opening to actuate the pair of jaws or shears 120, 130 between a "resting" open position and a closed position. In one aspect, spring forces may bias the pair of jaws or shears 120, 130 toward the "resting" opening position and actuation may be required to close the pair of jaws or shears 120, 130. In one aspect, the trigger handle 320 of the handle assembly 300 may be in a released state and the scissors end effector assembly 100 may be considered to be in the "resting" open position, where the pair of shears 120, 130 are biased open relative to on another.

The actuation to close the pair of jaws or shears 120, 130 may include pulling the trigger handle 320 of the handle assembly 300 to act against the spring forces, thereby forcing the needle tip 170 over cam profile surfaces associated with each of the jaws or shears 120, 130, as will be described in further detail below. Such an actuation configuration may help reduce or eliminate backlash associated with scissors end effectors in the related art. In one aspect, the scissors end effector assembly 100 may be manufactured as part of a surgical instrument or may be manufactured individually and inserted into a hub 310 of a surgical instrument or handle assembly 300 as needed.

As shown in FIG. 1, the handle assembly 300 may be in the form of a single use or a reusable handle, and may include the hub 310 for attaching various end effector assemblies, including the scissors end effector assembly 100. The cannula 110 of the scissors end effector assembly 100 may define an interior lumen, and may have a diameter of about 1 mm to about 5 mm, thereby reducing trauma to the patient and eliminates the need for a larger incision point or for a series of small incision cuts through the various layers of fascia. The incision point on the patient may be 5 mm or less depending on the diameter of the needle tip 170. In one aspect, the diameter of the cannula 110 may be 3 mm or less, and may be between 2.0 mm and 2.95 mm, for example, to reduce trauma, reduce scarring, and improve recovery time.

The scissors end effector assembly 100 may be configured to provide an electrocautery function, and the cannula 110 may include electrical insulation on an outer surface. For example, an outer surface of the cannula 110 may be wrapped and/or coated with an insulating plastic or other material that is compatible for insertion into a human cavity. In one aspect the insulation may be in the form of heat shrink insulation 112, and may include shrink stop 114 to prevent a lock hub from advancing beyond the shrink stop 114. The scissors end effector assembly 100 may further be specified with certain heat parameters to withstand heat levels associated with the electrocautery, as will be appreciated by one skilled in the art in view of the present disclosure.

Figure 4:
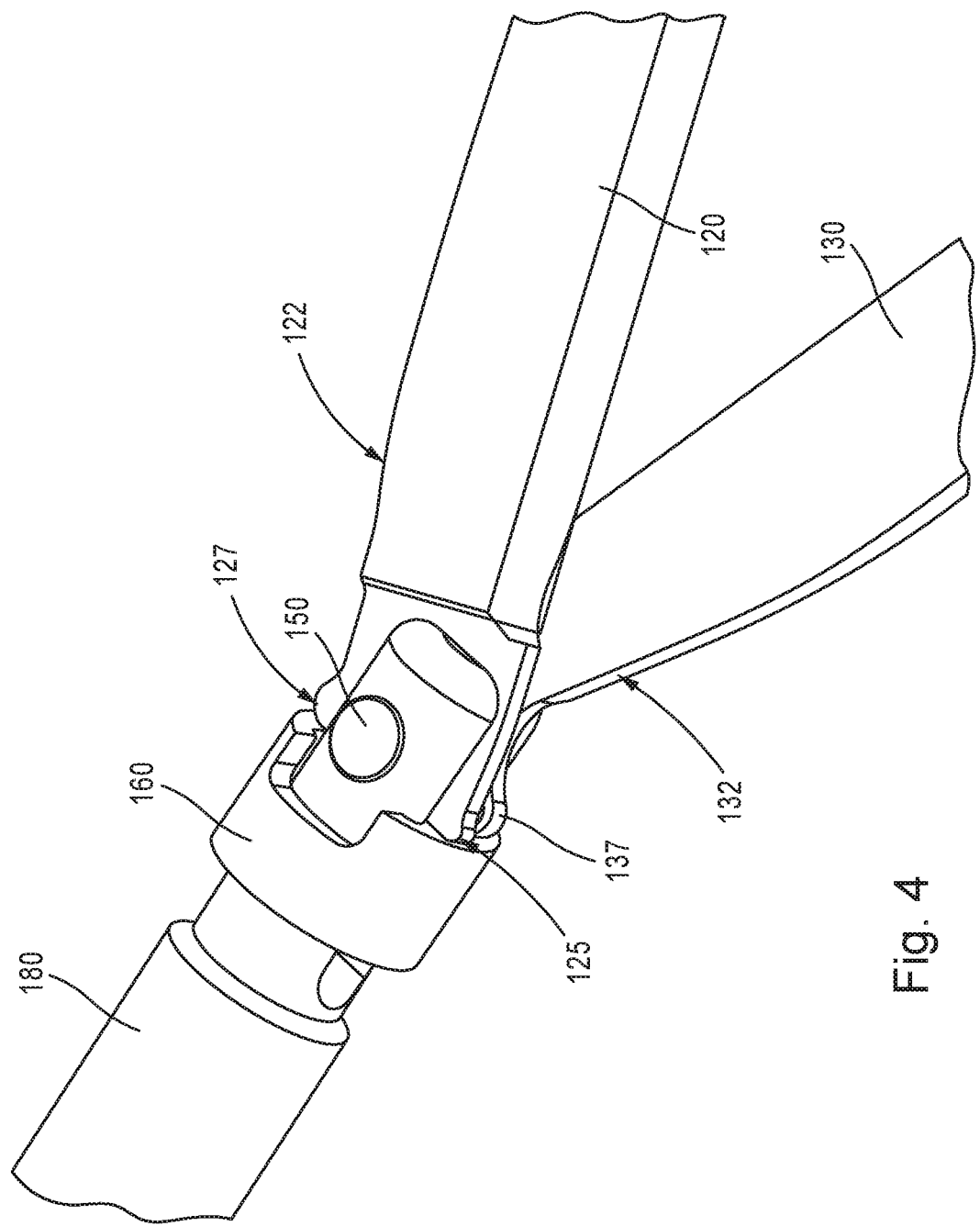
FIG. 4 shows a third enlarged perspective view of the scissors end effector assembly of FIG. 1 in accordance with aspects of the disclosure.
Figure 5:
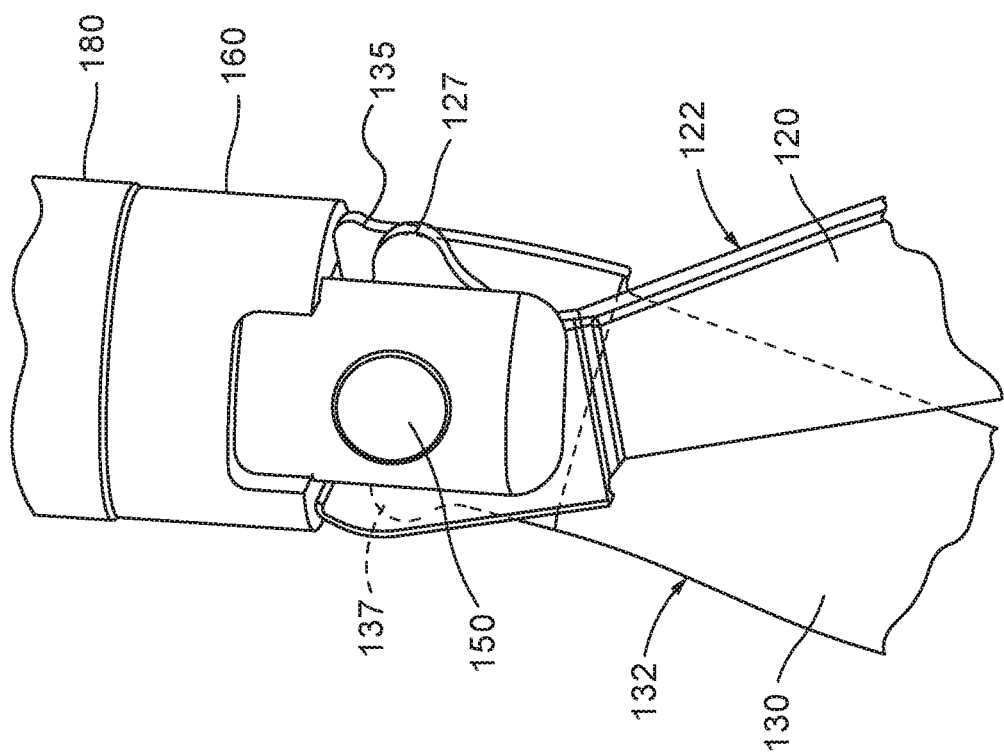
FIG. 5 shows a fourth enlarged perspective view of the scissors end effector assembly of FIG. 1 in accordance with aspects of the disclosure.
Figure 6:
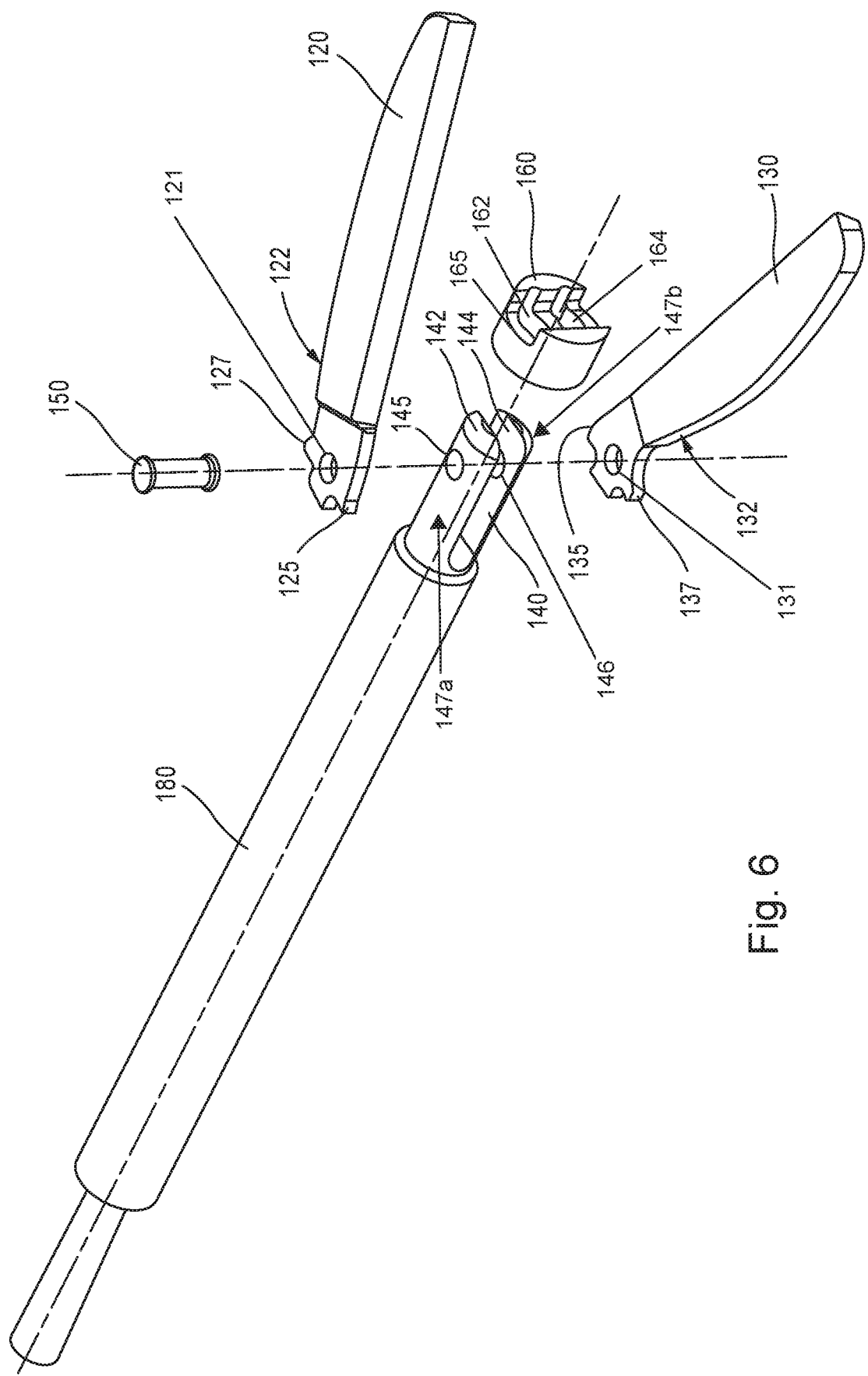
FIG. 6 shows an assembly view of the scissors end effector assembly of FIG. 1 in accordance with aspects of the disclosure.

Referring to FIGS. 2-6, a distal end of the scissors end effector assembly 100 in the open position is shown. The scissors end effector assembly 100 may include the pair of jaws or shears 120, 130, a clevis 140, a fastener 150, a cam bushing 160, and a cam tube 180. As shown in FIG. 6, the clevis 140 may include an upper arm 142 and a lower arm 144. Each of the upper and the lower arms 142, 144 may define at least one mounting hole 145, 146 configured to receive the fastener 150. The clevis 140 may be attached to a distal end of the cam tube 180. In one aspect, the clevis 140 may be formed integrally with the cam tube 180. For example, clevis 140 may be formed together with the cam tube 180, or may be machined from the cam tube 180. The upper and lower arms 142, 144 of the clevis 140 may extend parallel to a longitudinal axis of the cam tube 180. In one aspect, the upper and lower arms 142, 144 may define semi-cylindrical outer surfaces 147a, 147b. The semi-cylindrical outer surfaces 147a, 147b extend from the longitudinal axis of the cam tube 180, and the extension may be defined by a first effective radius distance. In one aspect, the first effective radius distance is less than a radius of an outer cylindrical surface 182 of the cam tube 180.

Figure 2:
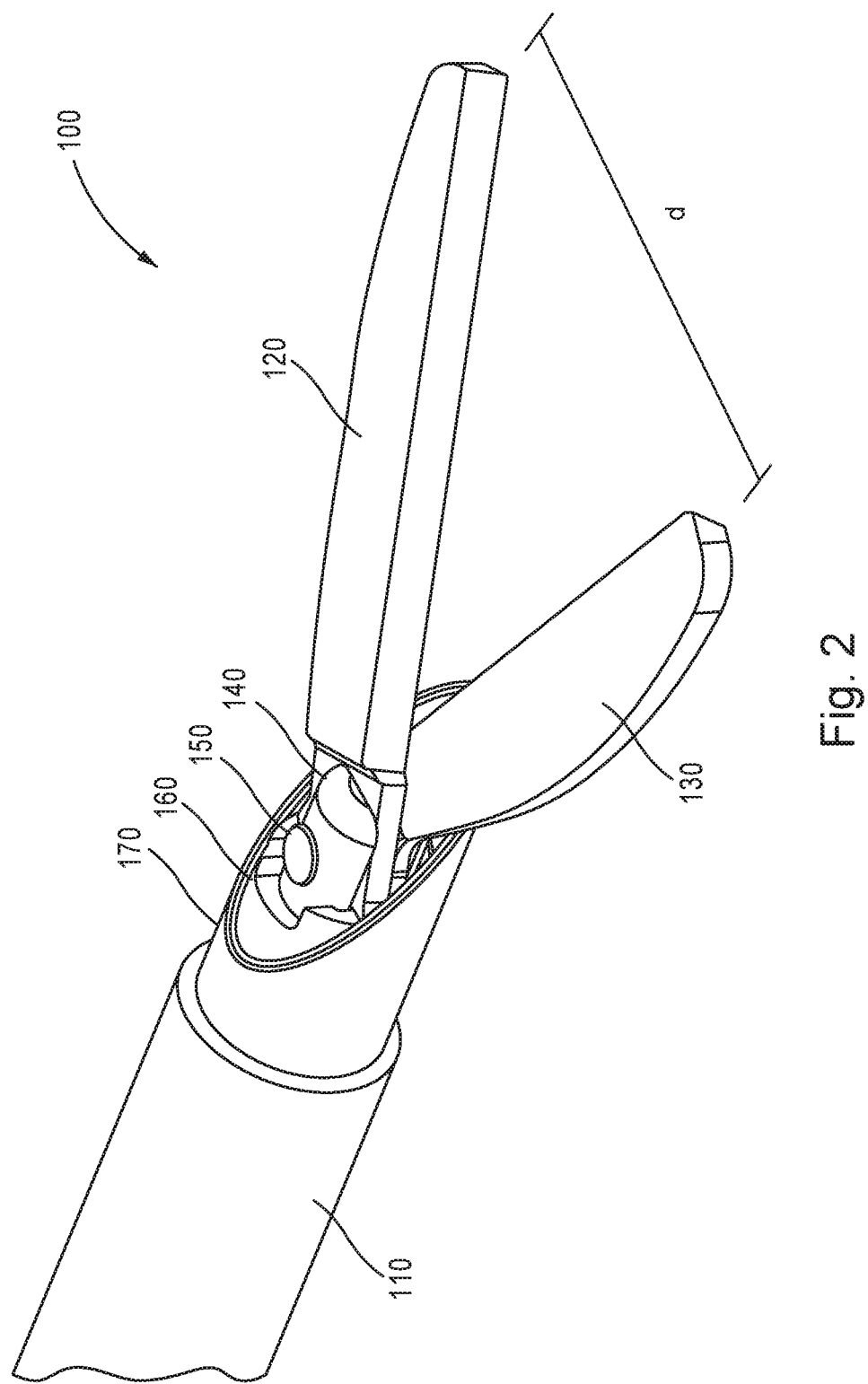
FIG. 2 shows a first enlarged perspective view of the scissors end effector assembly of FIG. 1 in accordance with aspects of the disclosure.
Figure 3:
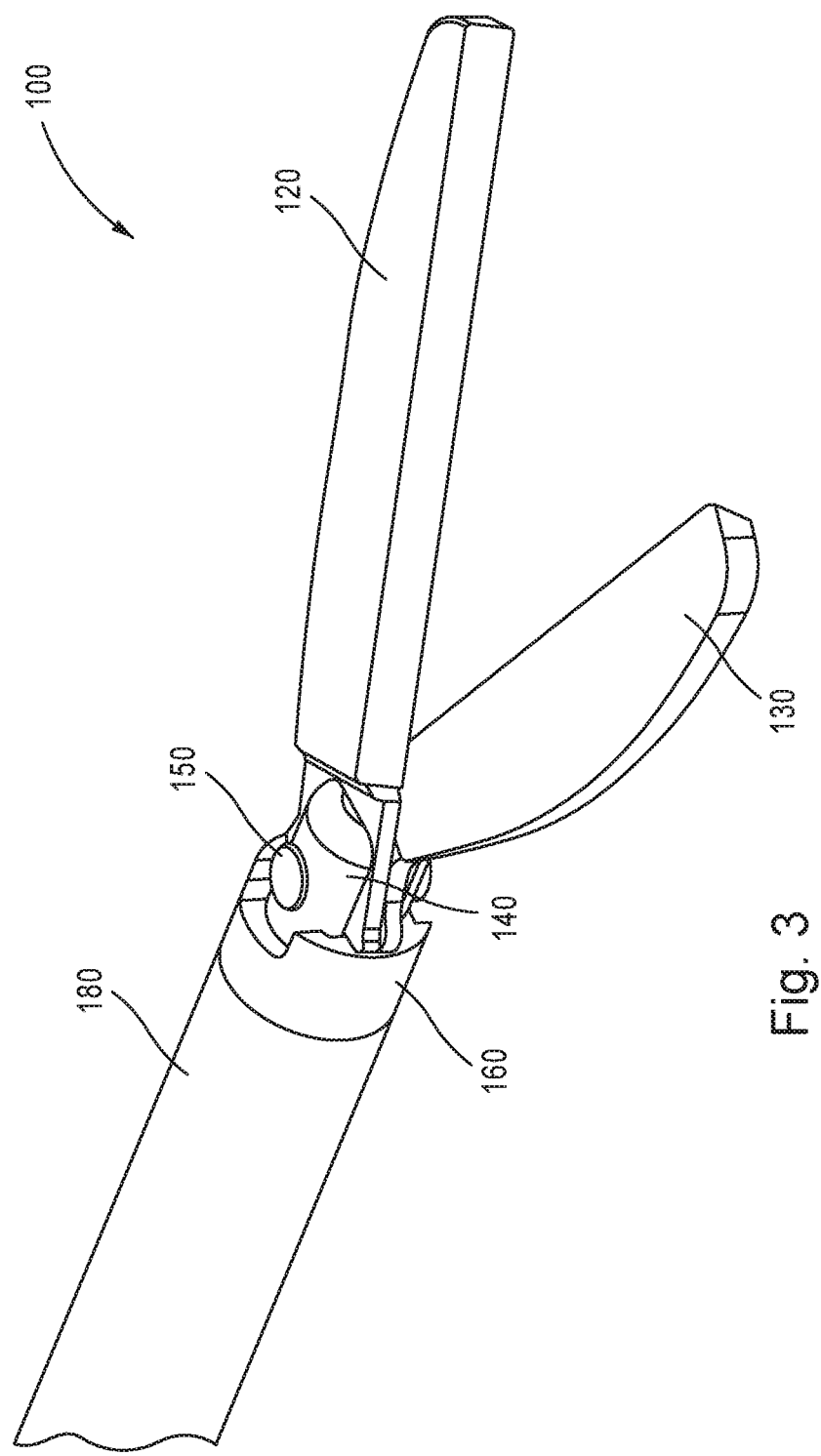
FIG. 3 shows a second enlarged perspective view of the scissors end effector assembly of FIG. 1, with the cannula and needle tip hidden, in accordance with aspects of the disclosure.

As shown in FIGS. 2-3, the pair of jaws or shears 120, 130 may be biased away from each other when extended from the needle tip 170. In one aspect, distal ends of the pair of jaws or shears 120, 130 may be placed in the open position, up to a predetermined maximum distance, in preparation for a cutting procedure. In one aspect, the predetermined maximum distance (d) between the distal ends of the pair of jaws or shears 120, 130 in the opened position is up to 30 mm. In one aspect, the predetermined maximum distance (d) is between 10 mm to 25 mm. In one aspect, inner cutting surfaces of the pair of jaws or shears 120, 130 may be beveled and/or serrated in order to promote cutting or shearing of tissue as the pair of jaws or shears 120, 130 are moved from the open position to the closed position.

When the needle tip 170 is extended over the jaws or shears 120, 130, in the closed position, the needle tip 170 may be used to insert the scissors end effector assembly 100 through a patient's fascia, body wall, and into a body cavity such that a trocar is not necessary. When the needle tip 170 is actuated to extend over the jaws or shears 120, 130, by actuating the needle tip 170 in a distal direction relative to the handle assembly 300 and/or actuating the pair of jaws or shears 120, 130 in a proximal direction relative to the handle assembly 300, the pair of jaws or shears 120, 130 may be forced to collapse towards each other and close. In this state, the scissors end effector assembly 100 may advantageously be capable of self-inserting, and the needle tip 170 may be used to form an incision into the fascia of the patient to reduce the number of surgical steps and to reduce the overall surgery time. Additionally, the scissors end effector assembly 100, including the needle tip 170, may be used to penetrate into the body cavity of the patient without a trocar to create an incision point that is 5 mm or less, depending on an outer diameter of the needle tip 170, thereby reducing trauma to the patient and eliminating the need for a larger incision point. In one aspect, the outer diameter of the needle tip 170 may be less than 3 mm, and preferably between about 2.0 mm to 2.95 mm.

As shown in FIGS. 4-6, the cam bushing 160 may be slidably mounted on a distal end of the clevis 140. The cam bushing 160 may define upper and lower slots 162, 164 with openings corresponding to a cross section of the upper and lower arms 142, 144, respectively. The cam bushing 160 may be configured to slide along a longitudinal direction, parallel to the longitudinal axis of the cam tube 180, and may be rotationally constrained by the clevis 140 via the upper and lower arms 142, 144. The cam bushing 160 and the cam tube 180 may be forced or biased forward toward the distal direction, relative to the handle assembly 300, by the use of a spring 190 (shown in FIGS. 7 and 8), which in turn forces the pair of jaws or shears 120, 130 to open via a top cam lobe 125 and a bottom cam lobe 135, respectively. The top cam lobe 125 and the bottom cam lobe 135 are disposed on proximal portions of the jaws or shears 120, 130, respectively, and extend toward the inner cutting surfaces of the jaws or shears 120, 130. The pair of jaws or shears 120, 130 may include a top open stop 127 and a bottom open stop 137, respectively, to prevent the pair of jaws or shears 120, 130 from opening beyond a maximum predetermined angle of opening, and may therefore serve as a safety measure. The top open stop 127 and the bottom open stop 137 may contact the cam bushing 160 to limit a maximum opening angle of the pair of jaws or shears 120, 130. The top open stop 127 and the bottom open stop 137 may be disposed on proximal portions of the jaws or shears 120, 130, respectively, and may extend away the inner cutting surfaces of the jaws or shears 120, 130. In other words, the top open stop 127 and the bottom open stop 137 may be disposed opposite of the top cam lobe 125 and the bottom cam lobe 135, respectively.

The cam bushing 160 may further define a notched portion 165 which may provide clearance for installation and assembly of the pair of jaws or shears 120, 130 to the clevis 140 via the fastener 150. Additionally, the notched portion 165 may allow the cam bushing 160 to slide relative to the clevis 140 without interfering with the fastener 150 and a pivot point of the pair of jaws or shears 120, 130, thereby promoting a more compact design capable of use in needlescopic surgical applications.

As shown in FIGS. 4 and 5, outer facing surfaces of the pair of jaws or shears 120, 130 may include closing cam profile surfaces 122, 132, respectively. In one aspect, as the pair of jaws or shears 120, 130 are retracted proximally relative to the needle tip 170, a beveled edge of the needle tip 170 may contact and ride along the closing cam profile surfaces 122, 132, thereby causing the pair of jaws or shears 120, 130 to close in order to perform a cutting operation, and/or to retract within the needle tip 170. When the pair of jaws or shears 120, 130 are fully retracted within the needle tip 170, the scissors end effector assembly 100 may be inserted into or removed from the body cavity of the patient.

In operation, the needle tip 170 may be extended or advanced to drive the pair of jaws or shears 120, 130 toward each other to cut any tissue, sutures, and the like, by overcoming a cam bushing force. In other words, a distance between the handle assembly 300 and the pivot of the pair of jaws or shears 120, 130 may be fixed, and the cannula 110 and the needle tip 170 may be advanced in a distal direction to close the pair of jaws or shears 120, 130, or advanced in a proximal direction to open the pair of jaws or shears 120, 130. The fixed position of the pair of jaws or shears 120, 130 relative to the handle assembly 300 provides the surgeon with a more predictable cutting actuation, while also enabling the scissors end effector assembly 100 to serve as a percutaneous instrument. In one aspect, actuation of the trigger handle 320 may drive the needle tip 170 in a distal direction to override a force of the cam spring 190, and the force of the cam spring 190 may result in a stronger cutting force for the jaws or shears 120, 130. The trigger handle 320 may subsequently be released, allowing the needle tip to be retracted and the cam busing force may once again force the pair of jaws or shears 120, 130 apart into the open position.

Figure 9:
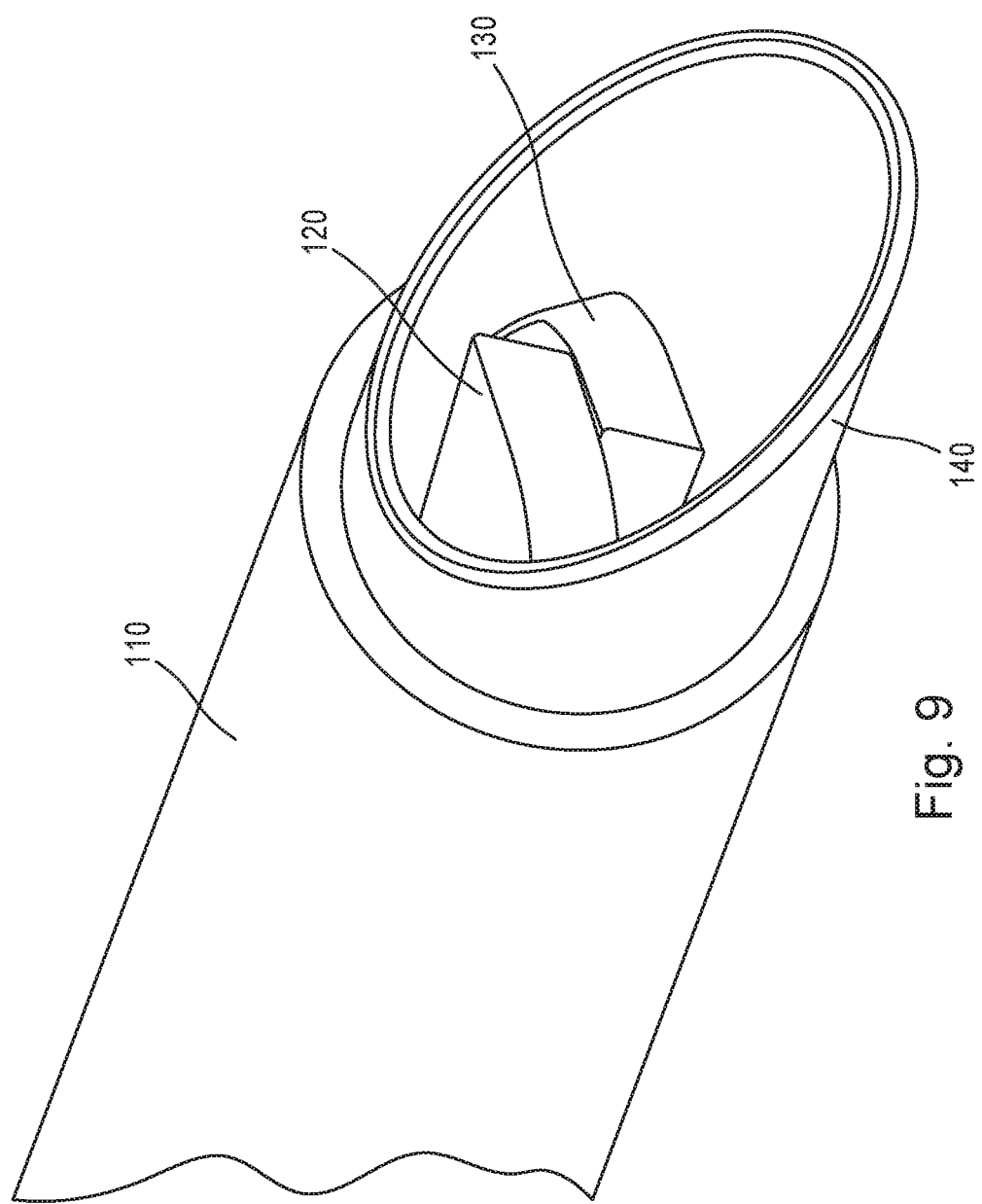
FIG. 9 shows a perspective view of a distal end of the scissors end effector assembly of FIG. 1, actuated with the jaws in a closed position and retracted within the needle tip, in accordance with aspects of the disclosure.

In one aspect, the closing cam profile surfaces 122, 132 may be provided with complementary profiles such that both jaws or shears 120, 130 may be actuated simultaneously and remain in contact with the needle tip 170 throughout their respective strokes. In one aspect, the closing cam profile surfaces 122, 132 remain in constant contact with the needle tip 170 between at least the open position and the closed position to reduce or eliminate any backlash effect. Because the pair of jaws or shears 120, 130 are stacked side by side in the closed position (as shown in FIG. 9) and contact needle tip 170 at different locations, the closing cam profile surface 122 of the top jaw or shear 120 and the closing cam profile surface 132 of the bottom jaw or shear 130 may have asymmetrical geometry even though their respective actuation motion may complement each other.

In one aspect, outer edges of each pair of the pair of jaws or shears 120, 130 may be maintained in constant contact with the needle tip 170 via the cam bushing force, which may promote minimal (if any) backlash, leading to no loss of motion or delay when the surgeon switches between the open position and the closed position of the scissors. As such, the surgeon can perform more accurate cutting, with more precise action, and therefore leads to quicker and shorter surgical time.

As shown in FIG. 6, the scissors end effector may be assembled by inserting the cam bushing 160 over the upper and lower arms 142, 144 of the clevis 140 in a proximal direction. The pair of jaws or shears 120, 130 may each define a mounting hole 121, 131 on a proximal end. The pair of jaws or shears 120, 130 may be inserted between the upper and lower arms 142, 144 of the clevis 140, and the mounting holes 121, 131 may be aligned with the mounting holes 145, 146 of the clevis 140. Once aligned, the fastener 150 may be inserted through the mounting holes 121, 131 of the pair of jaws or shears 120, 130, and through the mounting holes 145, 146 of the clevis 140. The fastener 150 may then be secured or locked to prevent disassembly of the pair of jaws or shears 120, 130 from the clevis 140 while enabling the jaws or shears 120, 130 to pivot or rotate about a central axis of the fastener 150. The central axis of the fastener 150 may be oriented perpendicular to the longitudinal axis of the cam tube 180 (as shown in FIG. 6). In one aspect, the fastener 150 may be a screw, pin, rivet or tube, as will be appreciated by one skilled in the art in view of the present disclosure.

Figure 7:
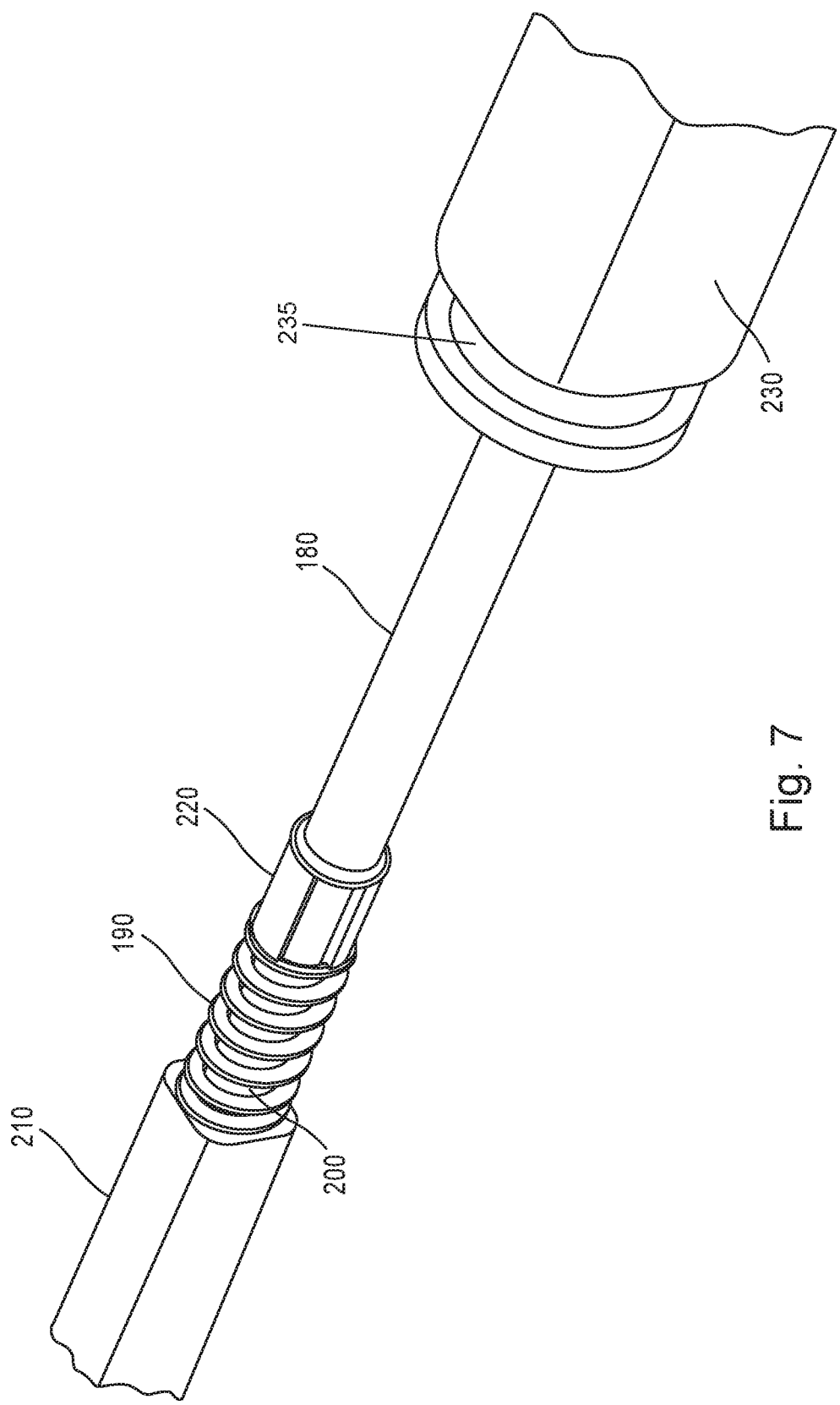
FIG. 7 shows a perspective view of a proximal end of the scissors end effector assembly of FIG. 1 in accordance with aspects of the disclosure.
Figure 8:
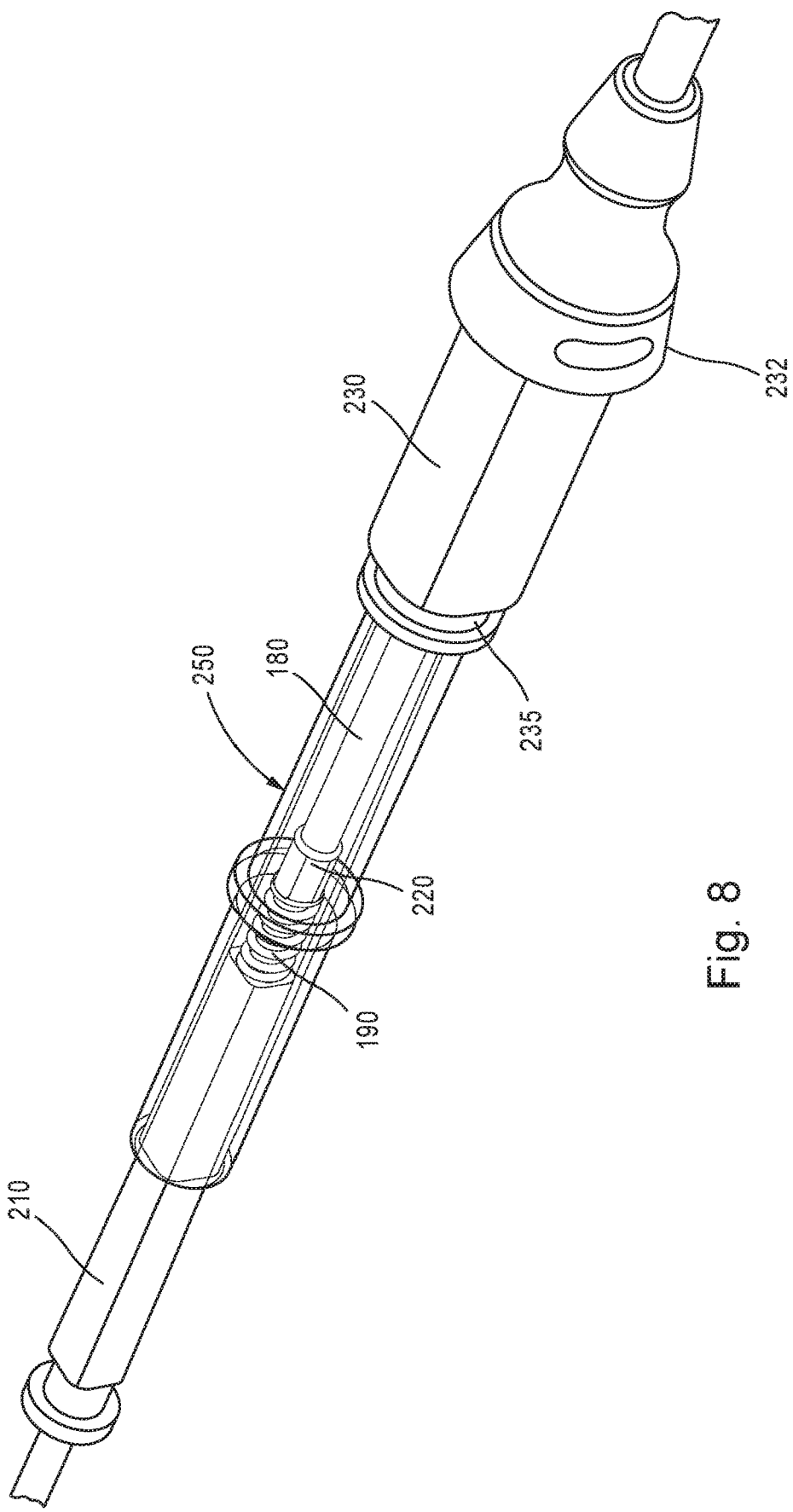
FIG. 8 shows a perspective view of a proximal end of the scissors end effector assembly of FIG. 1, with a needle hub attached, in accordance with aspects of the disclosure.

FIGS. 7 and 8 show the cam spring 190 which may be used to keep and/or to bias the pair of jaws or shears 120, 130 toward the open position by applying a force to the cam bushing 160 and the cam lobes 125, 135. The cam spring 190 may be positioned at a proximal end of the cam tube 180 and may be held in place with a standoff collar 220. The cam spring 190 may be installed over a rod 200, and the rod 200 may extend between a rod hub 210 and the standoff collar 220. As shown in FIGS. 7 and 8, the standoff collar 220 may be secured to a proximal end of the cam tube 180. In one aspect, a lock hub 230 may be provided to secure the scissors end effector assembly 100 to the handle assembly 300. In one aspect, the hub 310 of the handle assembly 300 may include at least one inwardly extending protrusion or latch which is operable to engage a slot defined by a lock collar flange 235 of the lock hub 230. The lock hub 230 may include an interior lumen, and the cam tube 180 may extend through the lock hub 230 towards the distal end of the scissors end effector assembly 100. The cam tube 180 may translate in a longitudinal direction within the interior lumen of the lock hub 230, and an amount of travel of the cam tube 180, relative to the lock hub 230, may be limited by a travel of the cam spring 190.

As discussed above, the pair of jaws of shears 120, 130 may be closed by moving the needle tip 170 over cam profile surfaces 122, 132 associated with each of the jaws or shears 120, 130. In one aspect, as shown in FIG. 9, the pair of jaws or shears 120, 130 may be fully housed within the needle tip 170. In this position, the needle tip 170 may be fully extended or advanced over the pair of jaws or shears 120, 130. In one aspect, the needle tip may be placed in the fully extended or advanced by exceeding the force of the cam spring 190. For example, the trigger handle 320 may be actuated by the surgeon to act against the force of the cam spring 190. When the pair of jaws or shears 120, 130 is fully housed within the extended needle tip 170, the needle tip 170 of the scissors end effector assembly 100 may be used as a puncturing tip to be inserted into the patient's fascia, body wall, and/or body cavity. Additionally, or alternatively, when the pair of jaws or shears 120, 130 is fully housed within the extended needle tip 170, the scissors end effector assembly 100 may be withdrawn from the patient without widening the incision. In one aspect, the extended needle tip 170 may be used during surgery, while inserted into the body cavity, to puncture an organ or tumor, such as a gall bladder for drainage.

Figure 10:
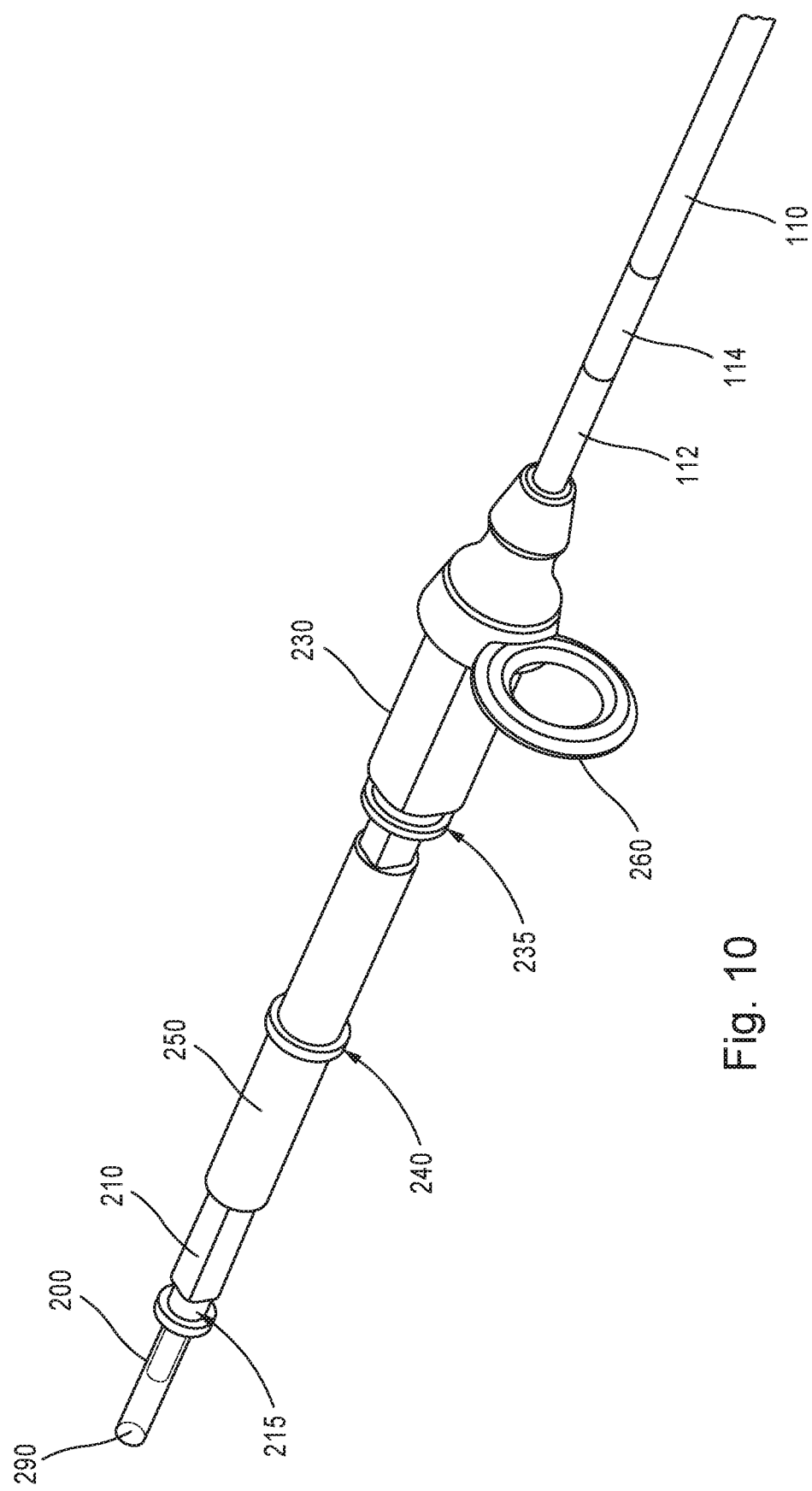
FIG. 10 shows a perspective view of a proximal end of the scissors end effector assembly of FIG. 1, in accordance with aspects of the disclosure.

FIG. 10 shows the proximal end of the scissors end effector assembly 100, in accordance with aspects of the present disclosure. In one aspect, the cannula 110 may be covered with heat shrink insulation. In one aspect, the lock hub 230 may be provided with a lock pin 26, and the lock pin 260 may be used for stabilization during shipping of the scissors end effector assembly 100. In one aspect, the lock collar flange 235 of the lock hub 23 may assist in locking the scissors end effector assembly 100 onto the handle assembly 300 of the surgical instrument 10. Furthermore, locking mechanism for the handle assembly 300 may include a needle hub flange lock 240, which may extend radially from the needle hub 250. A further locking mechanism may be provided in the form of a rod hub flange 215 disposed on a proximal end of the rod hub 210. Each of the above flanges may assist in securing the scissors end effector assembly 100 onto the handle assembly 300 of the surgical instrument 10, regardless of whether the handle assembly 300 is a reusable handle or a single-use handle, and regardless of whether the handle assembly 300 is a plunger style or a pistol grip style.

In one aspect of the present disclosure, the scissors end effector assembly 100 may be an electrocautery, and may be utilized to cauterize any dissected or cut tissue in a single procedure. For example, the scissors end effector assembly 100 may be equipped with electrocautery, the scissors end effector assembly 100 may be inserted into a mono polar or bipolar surgical instrument, which may include the necessary electrical components and connections to transmit the necessary electrosurgical energy needed for cauterizing target tissue using the pair of jaws or shears 120, 130. In one aspect, the scissors end effector assembly 100 may include a contact post 290 (shown in FIG. 10). The surgeon may dissect or cut certain tissue, and then apply electrosurgical energy through the scissors end effector assembly 100 to cauterize the target tissue. A typical electrosurgical treatment instrument may be capable of treating tissue with the use of heat produced by electrical energy while cutting, shearing, or contacting the target tissue. As such, the scissors end effector assembly 100 may be used to carry out treatments such as incision, coagulation, and the like. The scissors end effector assembly 100 may include an active electrode and an inactive, so-called neutral electrode. If monopolar, then during the whole duration of the surgery, the neutral electrode may be electrically connected to a large area of skin of the patient, for example, at the thigh or at the upper arm.

An exemplary method of using the scissors end effector assembly 100 will now be discussed. The method may comprise providing the handle assembly 300 including the hub 310 and the trigger handle 320, and providing the scissors end effector assembly 100. The scissors end effector assembly 100 may include the pair of jaws or shears 120, 130, the clevis 140, the fastener 150, the cam bushing 160, the needle tip 170, and the cam tube 180. In instances where the scissors end effector assembly 100 and the handle assembly 300 are sold and/or packaged separately, the method may comprise a set of attaching the scissors end effector assembly 100 to the handle assembly 300, the attaching including inserting at least the cam tube 180 of the scissors end effector assembly 100 into the hub 310 of the handle assembly 300. Once assembled, the pair of jaws or shears 120, 130 may be biased in the open position.

The method of using the scissors end effector assembly 100 may comprise actuating the trigger handle 320 to advance the needle tip 170 over the pair of jaws or shears 120, 130 to place the pair of jaws or shears 120, 130 in the closed position. The actuating may include completely advancing the needle tip 170 over the pair of jaws or shears 120, 130 so as to reveal a sharp beveled surface of the needle tip 170. In one aspect, the method may include locking a position of the trigger handle 320 and/or the needle tip 170 to maintain a position of the needle tip relative to the pair of jaws or shears 120, 130, to prevent any inadvertent release of the pair of jaws or shears 120, 130 during a puncturing or insertion process.

The method may comprise puncturing and/or inserting the needle tip 170 through fascia and/or a body wall and into a body cavity such that the pair of jaws or shears 120, 130 are completely within the body cavity. The step may include forming an incision hole as the needle tip is inserted through the fascia and/or the body wall by applying force in a distal direction relative to the handle assembly 300. Once inserted into the body cavity, the method may include unlocking and/or releasing the trigger handle 320 to retract the needle tip 170 and to advance the pair of jaws or shears 120, 130 towards the open position. The method may include guiding the pair of jaws or shears 120, 130 toward target tissues, and cutting the target tissues by at least partially advancing the needle tip 170 over the pair of jaws or shears 120, 130. The cutting process may be repeated depending on a length of the target tissues, or if the target tissues are located at multiple locations. In one aspect, where cauterization is desired, electrosurgical energy may be applied through at least one of the jaws or shears 120, 130. In one aspect, the jaws or shears 120, 130 may be placed in the closed position, prior to performing a cauterization procedure, such that the jaws or shears 120, 130 are stacked side-by-side to prevent cutting during the cauterization procedure.

The method may include advancing the needle tip 170 over the pair of jaws or shears 120, 130 to place the pair of jaws or shears 120, 130 in the closed position. In the closed position, the scissors end effector assembly 100 may be withdrawn from the body cavity by applying force in a proximal direction relative to the handle assembly 300. The scissors end effector assembly 100 may be disassembled from the handle assembly 300. The scissors end effector assembly 100 and/or the handle assembly 300 may be disposed of, if they are designed for a single-use application, or they may be sterilized and reused. It will be appreciated be one skilled in the art, in view of the above, that not all of the above steps need to be performed, and that the steps may be performed in a different order than presented.

Figure 11:
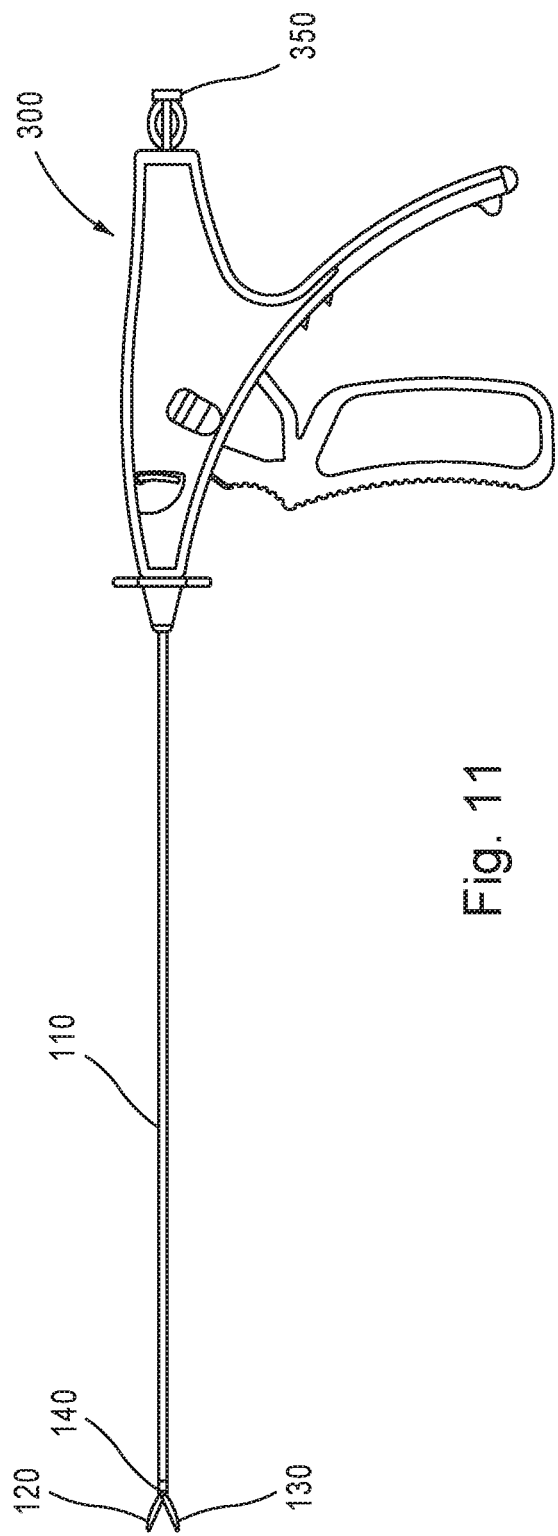
FIG. 11 shows a side view of an exemplary surgical instrument with an electrical connector in accordance with aspects of the disclosure.

In one aspect, the surgical instrument interface may further comprise an electrical connector for connecting a conductor to an external electrosurgical generator. As shown in FIG. 11, the handle assembly 300 may be provided with an electrical connector 350, and the electrical connector may be attached to the handle assembly 300 during manufacture. During use, electrical energy may be supplied to the surgical instrument 10 via a conventional electrosurgical generator (not shown), which may be activated by a user (e.g., surgeon) via a switch electrically connected to the electrosurgical generator. In one aspect, the switch may be in the form of a foot switch or pedal, and the electrosurgical generator may supply electrical energy through a power cord connected to the electrical connector 350 when the foot switch or pedal is activated or depressed. Typically a high frequency AC or RF current may be employed in electrocautery operations, with the voltage being dependent on the type and degree of treatment being performed. Voltages may typically be about 3000V for coagulation, but may be up to at least 12,000V for some applications.

In one aspect, the scissors end effector assembly 100 and the handle assembly 300 may come packaged together as a percutaneous surgical instrument kit, whereby the scissors end effector assembly 100 may be placed on and snapped onto the handle assembly 300 of the surgical instrument 10 prior to being packaged for shipment and/or sale. In one aspect, the scissors end effector assembly 100 and the handle assembly 300 may be packaged separately as stand-alone products and may be utilized whenever necessary.

Figure 12:
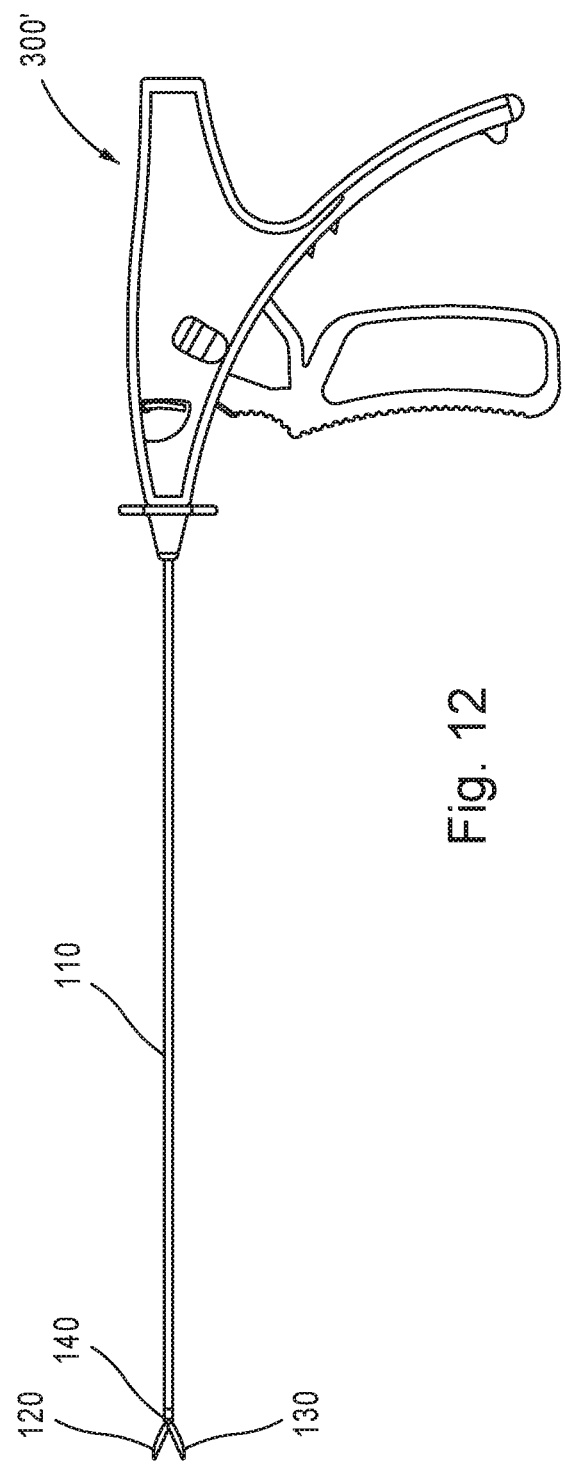
FIG. 12 shows a side view of an exemplary surgical instrument in accordance with aspects of the disclosure.

As shown in FIG. 12, the scissors end effector assembly 100 may be attached to the handle assembly 300' during manufacture and may be sold as either a single-use disposable surgical instrument, or a surgical instrument capable of re-sterilization and reuse. In one aspect, the scissors end effector assembly 100 may be assembled with the handle assembly 300' such that it is not capable of being disconnected from the handle assembly 300'.

In view of the above, the scissors end effector assembly 100 of the present disclosure provides scissors, such as needlescopic scissors, that eliminates or reduces backlash experienced by surgeons compared with scissors in the related art. The scissors end effector assembly 100 of the present disclosure further has the advantages of being compact for needlescopic applications, and the scissors end effector assembly 100 may have a diameter of 3 mm or less, and preferably 2.9 mm or less. The needle tip 170 may have percutaneous ability to enter a body cavity, and thus does not require entry through a trocar, thereby reducing trauma to the patient by using small incision points and possibly fewer incisions in aggregate during the surgical operation. For example, access insertion of the needle tip 170 may promote time-saving entry into a patient's body, such as into an abdominal cavity, and may eliminate single incision closure at the end of the surgical procedure. The scissors end effector assembly 100 of the present disclosure provides an ultra slim design with incisionless entry capabilities that may help reduce patient scarring.

Furthermore, the scissors end effector assembly 100 may include cam profile surfaces 122, 132 on respective outer edges of the pair of jaws or shears 120, 130 that interact with the needle tip 170 so as to prevent inadvertent closure of the pair of jaws or shears 120, 130 and inadvertent cutting of tissue. Other safety features of the scissors end effector assembly 100 include closure of the needle tip 170 of the pair of jaws or shears 120, 130, which adds force to the closing of the scissors, thereby allowing the jaws or shears 120, 130 to cut or shear the target tissue more forcibly. In one aspect, as the jaws or shears 120, 130 are closed, there is less occurrence of accidental needle trauma to the patient. In one aspect, the scissors end effector assembly 100 may include additional safety measures such as locking mechanisms maintained by the lock collar flange 235, the needle hub flange lock 240, and/or the rod hub flange 215.

The present disclosure contemplates that the scissors end effector assembly 100 will provide the following benefits, structures, and advantages: improved surgical precision, reduced surgical time resulting in reduced trauma to the patient, reduced scarring, reduced recovery time, reduced pain, easier handling and maneuverability by the surgeon via lack of backlash, and other benefits.

The scissors end effector assembly 100 may be used in a variety of laparoscopic procedures. The methods and systems of the present disclosure, as described above and shown in the drawings, provide minimally invasive surgical assemblies with superior properties including ease of assembly, use, and operation. While the apparatus and methods of the present disclosure have been shown and described, it will be appreciated that the foregoing description provides examples of the scissors end effector assembly, which may be used with a surgical instrument for minimally invasive surgery. However, it is contemplated that other implementations of the disclosure may differ in detail from the foregoing examples. All references to the disclosure or examples thereof are intended to reference the particular example being discussed at that point and are not intended to imply any limitation as to the scope of the disclosure more generally. All language of distinction and disparagement with respect to certain features is intended to indicate a lack of preference for those features, but not to exclude such from the scope of the disclosure entirely unless otherwise indicated.

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context.

What is claimed is:

1. A scissors end effector assembly comprising:
   a top shear;
   a bottom shear;
   a cam tube extending in a longitudinal direction, the cam tube having a proximal end and a distal end;
   a clevis attached to the distal end of the cam tube, the clevis including an upper arm and a lower arm; and
   a cam bushing defining an upper slot having a periphery surrounding and slidably receiving the upper arm, and a lower slot having a periphery surrounding and slidably receiving the lower arm,
   wherein the top shear and the bottom shear are pivotally mounted between the upper arm and the lower arm such that the top shear and the bottom shear open and close via force or bias from the cam bushing.

2. The scissors end effector assembly of claim 1, further comprising:
   a cannula defining an interior lumen, the cannula having a proximal end and a distal end; and
   a needle tip attached to the distal end of the cannula,
   wherein at least the cam tube is slidably mounted to translate within the interior lumen of the cannula.

3. The scissors end effector assembly of claim 2, further comprising:
   a standoff collar attached to the proximal end of the cam tube;
   a rod hub with a rod attached to a distal end of the standoff collar;
   a cam spring installed over the rod and disposed between the rod hub and the standoff collar; and
   a lock hub defining an interior lumen, the lock hub including a lock collar flange for securing the scissors end effector assembly to a handle of a surgical instrument,
   wherein a proximal end of the cam tube extends through the interior lumen of the lock hub to a connection point with the standoff collar.

4. The scissors end effector assembly of claim 2, wherein the top shear defines a top cam lobe disposed on a proximal portion of the top shear, the top cam lobe extending toward an inner cutting surface of the top shear,
   wherein the bottom shear defines a bottom cam lobe disposed on a proximal portion of the bottom shear, the bottom cam lobe extending toward an inner cutting surface of the bottom shear, and
   wherein the cam bushing contacts the top cam lobe and the bottom cam lobe, and a force applied by the cam bushing in a distal direction biases the top shear and the bottom shear toward an open position via the top cam lobe and the bottom cam lobe, respectively.

5. The scissors end effector assembly of claim 4, wherein the top shear defines a top open stop disposed on a proximal portion of the top shear, the top open stop extending away from the inner cutting surface of the top shear,
   wherein the bottom shear defines a bottom open stop disposed on a proximal portion of the bottom shear, the bottom open stop extending away from the inner cutting surface of the bottom shear, and
   wherein the top open stop and the bottom open stop contacts the cam bushing to limit a maximum opening angle of the top shear and the bottom shear.

6. The scissors end effector assembly of claim 4, wherein the top shear defines a first closing cam profile surface on an outer edge of the top shear, opposite of the inner cutting surface of the top shear, and wherein the bottom shear defines a second closing cam profile surface on an outer edge of the bottom shear, opposite of the inner cutting surface of the bottom shear.

7. The scissors end effector assembly of claim 6, wherein the first closing cam profile surface and the second closing cam profile surface contact at least a portion of the needle tip, and
wherein the top shear and the bottom shear are guided toward a closed position, via the first closing cam profile surface and the second closing cam profile surface as the top shear and the bottom shear are retracted within the needle tip.

8. The scissors end effector assembly of claim 6, wherein the first closing cam profile surface and the second closing cam profile surface are asymmetrical with respect to one another.

9. The scissors end effector assembly of claim 2, wherein the cannula has an outer diameter of 3 mm or less.

10. The scissors end effector assembly of claim 2, wherein the cannula is wrapped or coated with an insulating material.

11. The scissors end effector assembly of claim 1, wherein each of the upper arm and the lower arm defines a mounting hole on a distal end thereof,
wherein each of the top shear and the bottom shear defines a mounting hole on a proximal end thereof, and
wherein the mounting holes of the upper arm and the lower arm, and the mounting holes of the top shear and the bottom shear are secured together via at least one fastener.

12. A needlescopic surgical device comprising:
the scissors end effector assembly of claim 1; and
a handle assembly having a trigger handle pivotally attached to the handle assembly, and having a hub for receiving an end effector assembly, wherein at least the cam tube of the scissors end effector assembly is inserted into the hub of the handle assembly.

13. The needlescopic surgical device of claim 12, wherein the scissors end effector assembly further comprises:
a cannula defining an interior lumen, the cannula having a proximal end and a distal end; and
a needle tip attached to the distal end of the cannula,
wherein at least the cam tube is slidably mounted to translate within the interior lumen of the cannula.

14. The needlescopic surgical device of claim 13, wherein the cannula has an outer diameter of 3 mm or less.

15. The needlescopic surgical device of claim 12, wherein the scissors end effector assembly further comprises a lock hub with a lock collar flange attached, the lock hub defining an interior lumen for supporting a proximal end of the cam tube, and
wherein the hub of the handle assembly includes at least one at least one inwardly extending protrusion or latch to engage a slot defined by the lock collar flange.

16. The needlescopic surgical device of claim 12, wherein the top shear defines a top cam lobe disposed on a proximal portion of the top shear, the top cam lobe extending toward an inner cutting surface of the top shear,
wherein the bottom shear defines a bottom cam lobe disposed on a proximal portion of the bottom shear, the bottom cam lobe extending toward an inner cutting surface of the bottom shear, and
wherein the cam bushing contacts the top cam lobe and the bottom cam lobe, and a force applied by the cam bushing in the distal direction biases the top shear and the bottom shear toward an open position via the top cam lobe and the bottom cam lobe, respectively.

17. The needlescopic surgical device of claim 16, wherein the top shear defines a top open stop disposed on a proximal portion of the top shear, the top open stop extending away from the inner cutting surface of the top shear,
wherein the bottom shear defines a bottom open stop disposed on a proximal portion of the bottom shear, the bottom open stop extending away from the inner cutting surface of the bottom shear, and
wherein the top open stop and the bottom open stop contacts the cam bushing to limit a maximum opening angle of the top shear and the bottom shear.

18. The needlescopic surgical device of claim 16, wherein the top shear defines a first closing cam profile surface on an outer edge of the top shear, opposite of the inner cutting surface of the top shear, and
wherein the bottom shear defines a second closing cam profile surface on an outer edge of the bottom shear, opposite of the inner cutting surface of the bottom shear.

19. The needlescopic surgical device of claim 18, wherein the first closing cam profile surface and the second closing cam profile surface are asymmetrical with respect to one another.

20. A method of using the scissors end effector assembly of claim 1 further including a fastener and a needle tip, the method comprising:
inserting at least the cam tube of the scissors end effector assembly into a hub of a handle assembly;
actuating a trigger handle of the handle assembly to advance the needle tip over the top and bottom shears and to place the top and bottom shears in a closed position;
puncturing, with the needle tip, through a body wall and into a body cavity such that at least the top and bottom shears are within the body cavity;
retracting the needle tip to move the top and bottom shears towards an open position; and
cutting a target by at least partially advancing the needle tip over the top and bottom shears and moving the top and bottom shears from the open position toward the closed position.

* * * * *